United States Patent [19]
Stemmer

[11] Patent Number: 6,096,548
[45] Date of Patent: *Aug. 1, 2000

[54] METHOD FOR DIRECTING EVOLUTION OF A VIRUS

[75] Inventor: Willem P. C. Stemmer, Los Gatos, Calif.

[73] Assignee: Maxygen, Inc., Redwood City, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/792,409

[22] Filed: Feb. 3, 1997

Related U.S. Application Data

[63] Continuation of application No. 08/621,430, Mar. 25, 1996, abandoned.

[51] Int. Cl.[7] ............................. C12N 15/00; C12P 19/34
[52] U.S. Cl. ......................................... 435/440; 435/91.2
[58] Field of Search ............................... 435/69.1, 172.3, 435/235.1, 252.3, 91.1, 91.2, 440

[56] References Cited

U.S. PATENT DOCUMENTS

| | | | |
|---|---|---|---|
| 5,811,238 | 9/1998 | Stemmer et al. | 435/6 |
| 5,830,721 | 11/1998 | Stemmer et al. | 435/489 |
| 5,834,252 | 11/1998 | Stemmer et al. | 435/91.1 |
| 5,939,250 | 8/1999 | Short | 435/4 |
| 5,958,672 | 9/1999 | Short | 435/4 |
| 5,965,408 | 10/1999 | Short | 435/91.1 |

FOREIGN PATENT DOCUMENTS

| | | |
|---|---|---|
| WO 93/25682 | 12/1993 | WIPO . |
| WO 95/22625 | 8/1995 | WIPO . |
| WO 95/34648 | 12/1995 | WIPO . |
| WO 96/00294 | 1/1996 | WIPO . |
| WO 97/10330 | 3/1997 | WIPO . |
| WO 97/20078 | 6/1997 | WIPO . |
| WO 97/35966 | 10/1997 | WIPO . |

OTHER PUBLICATIONS

De Vries et al. (Oct. 1984) Proc. Natl. Acad. Sci. USA 81:6080–6084.

Barrett et al., "Genotypic analysis of multiple loci in somatic cells by whole genome amplification," *Nuc. Acids Res.*, 23(17):3488–3492 (1995).

Crameri et al., "Improved Green Flourescent Protein by Molecular Evolution Using DNA Shuffling," *Nature Biotechnology*, 14:315–319 (Mar. 14, 1996).

Jensen et al., "Programmed cell death in bacteria: proteic plasmid stabilization systems," *Molecular Microbio.*, 17(2):205–210 (1995).

Levichkin et al., "A New Approach to Construction of Hybrid Genes: Homolog Recombination Method," *Molecular Biology*, 29(5), part 1:572–577 (1995).

Stemmer, "DNA Shuffling by Random Fragmentation and Reassembly: In Vitro Recombination for Molecular Evolution," *Proc. Natl. Acad. Sci. USA*, 91(22):10747–10751 (1994).

Stemmer, "Rapid Evolution of a Protein in Vitro by DNA Shuffling," *Nature*, 370:389–391 (1994).

Stemmer, "Searching Sequence Space, Using recombination to search more efficiently and thoroughly instead of making bigger combinatorial libraries," *Biotechnology*, 13:549–553 (1995).

Stemmer et al., "Single–Step Assembly of a Gene and Entire Plasmid From Large Numbers of Oligodeoxyribonucleotides," *Gene*, 164(1):49–53 (1995).

Stemmer, "The Evolution of Molecular Computation," *Science*, 270(5241):1510 (1995).

Crameri et al., "Combinatorial Multiple Cassette Mutagenesis Creates All the Permutations of Mutant and Wild–Type Sequences", *Biotechniques*, 18(2): 194–196 (Feb. 1, 1995).

Crameri et al., "Construction and evolution of antibody–phage libraries by DNA shuffling", *Nature Medicine*, 2(1): 100–102 (Jan. 1996).

Williams et al., "The Haemophilus Influenzae SXY–1 Mutations is in a Newly Identified Gene Essectial for Competence", Journal of Bacteriology, p. 6789–6794 (Nov. 1994).

*Primary Examiner*—Robert A. Schwartzman
*Attorney, Agent, or Firm*—Joe Liebeschuetz; Norman Kruse; Margaret A. Powers

[57] ABSTRACT

The invention provides a number of strategies for transferring and/or evolving gene(s) associated with cellular DNA uptake so that they confer or enhance DNA-uptake capacity of a recipient cell. Evolution is achieved by recursive cycles of recombination and screening/selection. One such strategy entails evolving genes that confer competence in one species to confer either greater competence in that species, or comparable or greater competence in a second species. Another strategy entails evolving genes for use as components of cloning vector to confer enhanced uptake of the vector. Other strategies entail evolving viral receptors, viruses, and genes that mediate conjugal transfer.

14 Claims, 9 Drawing Sheets ns US 6,096,548

1

METHOD FOR DIRECTING EVOLUTION OF A VIRUS

This is a Continuation of application Ser. No. 08/621,430, filed Mar. 25, 1996, now abandoned, the disclosure of which is incorporated by reference.

FIELD OF THE INVENTION

The invention applies the fields of classical and molecular genetics to the evolution of DNA sequences for facilitating cellular DNA uptake by a variety of mechanisms.

BACKGROUND OF THE INVENTION

Most procedures in molecular genetics require means for introducing nucleic acids into cells. This is usually accomplished by chemical transformation (e.g., $CaCl_2$ treatment), electroporation or, for *E. coli*, in vitro packaging of phage lambda. All of these methods are somewhat labor-intensive and time consuming, particularly, if a procedure requires many cycles of isolating, manipulating and transforming DNA. Furthermore, the efficiency of the procedures is relatively low. For example, even when transforming purified supercoiled DNA, at best, about 1/100 molecules become stably established in a cell. For ligation mixtures, the efficiencies are 2–3 orders of magnitude lower. Even these efficiencies are applicable to only a relatively small number of preferred cell types commonly used in genetic engineering. It would be desirable to be able to obtain high transfection efficiency in any cell of interest.

A few bacterial isolates are naturally competent (i.e., are capable of taking up DNA from their medium). Reports exist for Bacillus, Neisseria (Rudel et al., *PNAS* 92, 7986–7990 (1995); Facius & Meyer, *Mol. Microbiol.* 10, 699–712 (1993)); Haemophilus (Williams et al., *J. Bacteriol.* 176, 6789–6794 (1994)), Helicobacter (Haas et al., *Mol. Microbiol.* 8, 753–760 (1993)), Acinetobacter (Lorenz et al., *Arch. Microbiol.*, 157, 355–360 (1992)), Streptococcus (Lopez et al., *J. Gen. Microbiol.* 135, 2189–2197 (1989)), Campylobacter (Nedenskov-Sorensen, *J. Infect. Dis.* 161, 356–366 (1990)), Synechocystis (Barten & Lill, *FEMS Microbiol. Lett.* 129, 83–88 (1995)), Lactobacillus and Amycolatopis (Vrijbloed et al., *Plasmid* 34, 96–104 (1995)).

Some information has emerged concerning the genetic basis of natural competence in bacteria. Some genes have been identified and correlated with a role in mediating DNA uptake. In Neisseria, two proteins, PilC and PilE, having roles in phase variation, have been shown to be essential for natural competence (Rudel et al., *Proc. Natl. Acad. Sci. USA* 92, 7986–7990 (1995)). PilE is the major pilus subunit protein, and PilC functions in assembly and adherence of *gonococcal pili*. Both genes serve to convert linearized plasmid DNA into a DNase-resistant form. DNA uptake requires a Neisseria-specific uptake signal on the DNA and a functional RecA protein. DNA is taken up in linear form. Transformation with non-episomal DNA fragments requires homology to the chromosomal DNA to allow integration by homologous recombination. Other genes required for DNA uptake, called dud, and for transformation uptake, called ntr, have been identified (Biswas et al., *J. Bact.*, 171, 657–664 (1989)). In Haemophilus, the sxy gene has been reported to be essential for competence. Overexpression of the sxy gene product confers constitutive competence on wildtype Haemophilus cells, (Williams et al., *J. Bact.*, 176, 6789–6794 (1994)). In *E. coli*, the comA gene has been reported to be involved in natural competence (Facius & Meyer, *Mol. Microbiol.*, 10, 699–712 (1993)). Regulatory genes involved in competence are the homologs of the *E. coli* cya gene, encoding adenylate cyclase, and *E. coli* crp genes, encoding the cAMP receptor protein.

The present invention is generally directed to transferring genes conferring DNA-uptake capacity in one species to another and evolving the genes so that they also confer comparable or better DNA-uptake capacity in the second species and/or the original species. Genes are evolved by a process termed recursive sequence recombination which entails performing iterative cycles of recombination and screening/selection. Cells expressing the evolved genes can be transfected without undertaking the time consuming preparatory steps of prior methods and/or with greater efficiency than the cells of prior methods.

SUMMARY OF THE INVENTION

In a first embodiment, the invention provides methods of enhancing competence of a cell by iterative cycles of recombination and screening/selection. In the first cycle, at least first and second DNA segments from at least one gene conferring DNA competence are recombined. The segments differ from each other in at least two nucleotides. Recombination produces a library of recombinant genes. At least one recombinant gene is screened from the library that confers enhanced competence in the cell relative to a wildtype form of the gene. In the second cycle, at least a segment from one or more of the recombinant genes identified by screening is recombined with a further DNA segment from the gene conferring competence to produce a further library of recombinant genes. At least one further recombinant gene is screened from the further library of recombinant genes that confers enhanced competence in the cell relative to a previous recombinant gene. Further cycles of recombination and screening/selection are performed until a recombinant gene is produced that confers a desired level of enhanced competence in the cell.

Diversity between the first and second segments in the first cycle of recombination can result from generation of the second segment by error-prone PCR replication of the first segment or propagation of the first segment in a mutator strain. Alternatively, the second segment can be the same as the first segment except that a portion of the first is substituted with a mutagenic cassette.

In some methods, at least one recombining step is performed in vitro, and the resulting library of recombinants is introduced into the cell whose competence is to be enhanced generating a library of cells containing different recombinants. A typical in vitro recombining step entails: cleaving the first and second segments into fragments; mixing and denaturing the fragments; and incubating the denatured fragments with a polymerase under conditions which result in annealing of the denatured fragments and formation of the library of recombinant genes.

Often screening/selection identifies a pool of cells comprising recombinant genes conferring enhanced competence from the library. For example, selection can be achieved by transfecting a vector encoding a selective marker into the library of cells containing different recombinants, and selecting for cells expressing the selective marker. In some methods, the vector encoding the selective marker is a suicide vector.

In some methods, the further DNA segment in the second or subsequent round of recombination is a recombinant gene or library of such genes produced in a previous step. For example, the second or subsequent round of recombination can be performed by dividing the pool of cells surviving screening/selection into first and second pools. Recombinant genes are isolated from the first pool, and transfecting into the second pool where the recombinant genes from the first and second pools recombine to produce the further library of recombinant genes.

In some methods, at least one recombining step is performed in vivo, for example, by homologous recombination or by site-specific recombination. In vivo recombination can be performed, for example, by propagating a collection of cells, each cell containing a vector comprising an origin of transfer and a member of a recombinant gene library, and each cell expressing tra genes whose expression products conjugally transfer the vector between cells.

In some methods at least one of the DNA segments comprise a substantially complete genome. In some methods, each of the DNA segments comprises a cluster of genes collectively conferring DNA uptake capacity.

In a second embodiment, the invention provides a modified form of a cell, such as is producible by the above methods. The modification comprises the inclusion of an exogenous gene conferring enhanced competence relative to the cell. Suitable genes include stf or sxy. The exogenous gene is often from a different species than the cell.

In a third embodiment, the invention provides methods of enhancing transfection efficiency of a vector into a cell, which again involve iterative cycles of recombination and screening/selection. In the first recombination cycle, a DNA segment to be evolved for enhancing transfection efficiency is recombined with at least a second DNA segment, the at least a second DNA segment differing from the DNA segment in at least two nucleotides. Recombination produces a library of recombinant DNA segments. The library of recombinant DNA segments are then introduced into a population of cells as a component of a vector also containing a marker sequence. The cells are screened/selected for a subpopulation of the cells expressing the marker sequence. In the second and any subsequent rounds of recombination, at least one recombinant DNA segment from the subpopulation of cells is recombined with a further DNA segment, the same or different from the first and second segments, to produce a further library of recombinant DNA segments, which is transfected as a compound of recombinant vectors, each comprising a second marker sequence, the same or different from the first marker sequence, into a further population of cells. These cells are screened for a further subpopulation of cells expressing the marker sequence. Further cycles of recombination and screening/selection are then performed as necessary until a recombinant vector from one of the further libraries has a desired transfection efficiency in the cell.

In a fourth embodiment, the invention provides cell lines rendered susceptible to infection by a virus that is substantially unable to infect the cell line in nature. Susceptibility is conferred by introduction of an exogenous vector expressing a receptor of a virus on the cell surface. For example, the lamB viral receptor can be expressed on the surface of a cell other than *E. coli* to confer susceptibility to phage λ.

In a fifth embodiment, the invention provides methods of evolving a receptor of a virus to confer enhanced susceptibility to viral infection in a cell. These methods again involve cycles of recombination and screening/selection. In the first recombination cycle, a first DNA segment encoding the viral receptor or a fragment thereof is recombined with at least a second DNA segment, the segments differing from each other in at least two nucleotides, to produce a library of recombinant genes encoding recombinant viral receptors. A population of cells harboring the recombinant genes and expressing the viral receptors encoded by the recombinant genes on their surface can be infected with the virus and cells that become infected with the virus can be screened/selected. In the second and any subsequent rounds of recombination, at least one recombinant gene, or a fragment thereof, from the cells that become infected is recombined with a further DNA segment, the same or different from the first and second segments, to produce a further library of recombinant genes. The further DNA segment can itself be a recombinant gene or pool of such genes resulting from screening/selection. A second population of cells harboring the further library of recombinant genes and expressing the viral receptors encoded by the library on their surface is infected with the virus, and a further subpopulation of cells that become infected with the virus are screened/selected. Further rounds of recombination/screening are performed until a recombinant gene from a further library confers a desired susceptibility to viral infection in the cell. The methods can be used, for example, to evolve a viral receptor such that the receptor confers susceptibility to viral infection in a heterologous cell.

In a sixth embodiment, the invention provides methods of evolving a virus to increase the efficiency with which it infects a host cell. In a first cycle of recombination, a DNA segment from the virus to be evolved is recombined with at least a second DNA segment, the second DNA segment differing from the first DNA segment in at least two nucleotides, to produce a library of recombinant DNA segments. Host cells are then contacted with a collection of viruses having genomes including the recombinant DNA segments, and viruses that infect the host cells are identified by screening/selection. In a second round of recombination, at least one recombinant DNA segment from a virus infecting the host cells is recombined with a further DNA segment, the same or different from the first and second segments, to produce a further library of recombinant DNA segments. Additional host cells are contacted with a collection of viruses having genomes including the further recombinant DNA segments, and viruses that infect the additional host cells are identified by screening/selection. Further rounds of recombination and screening/selection are performed as necessary until a virus having a genome including a recombinant segment from a further library infects the host cells with a desired efficiency.

In a seventh embodiment, the invention provides methods of evolving a gene to confer enhanced conjugative transfer. In a first recombination step, at least first and second DNA segments from at least one conjugative transfer gene are recombined, the segments differing from each other in at least two nucleotides, to produce a library of recombinant genes. At least one recombinant gene from the library that confers enhanced conjugal transfer between cells relative to a wildtype form of the gene is identified by screening/selection. In a second round of recombination, at least a segment from the at least one recombinant gene is recombined with a further DNA segment from the at least one gene, the same or different from the first and second segments, to produce a further library of recombinant genes. At least one further recombinant gene from the further library of recombinant genes that confers enhanced conjugal transfer between cells relative to a previous recombinant gene is identified by screening/selection. Further cycles of recombination and screening/selection are performed until the further recombinant gene confers a desired level of enhanced conjugal transfer between cells.

In some methods of enhancing conjugal transfer of nucleic acids between cells, the first cycle of recombination is performed by propagating a collection of cells containing vectors comprising an origin of transfer, a marker sequence, and a library member sequence from a library of variant forms of a conjugative transfer gene, whereby the library member sequences conjugally transfer between cells and recombine with each other to generate vectors comprising recombinant library member sequences. Screening is performed by contacting the collection of cells with a second collection of cells and identifying cells from the second collection of cells that express the marker sequence. In the second round of recombination the cells identified in the previous screening step are propagated whereby recombinant library member sequences conjugally transfer between the cells and recombine with each other to generate vectors comprising further recombinant library member sequences. A second round of screening is performed by contacting the cells with a further collection of cells and identifying cells from the further collection of cells that express the marker sequence. Further rounds of recombination and screening/selection are performed as necessary until a further recombinant library member sequence is obtained conferring conjugal transfer with a desired efficiency.

BRIEF DESCRIPTION OF THE FIGURES

FIG. 5A. Selection for genes that allow stable establishment of a virus within the cell.

FIG. 5B. Selection for genes that allow productive viral infection.

FIG. 6A. Selection for viruses that stably establish within a cell.

FIG. 6B. Selection for viruses that productively infect a cell.

DEFINITIONS

Figure 1:
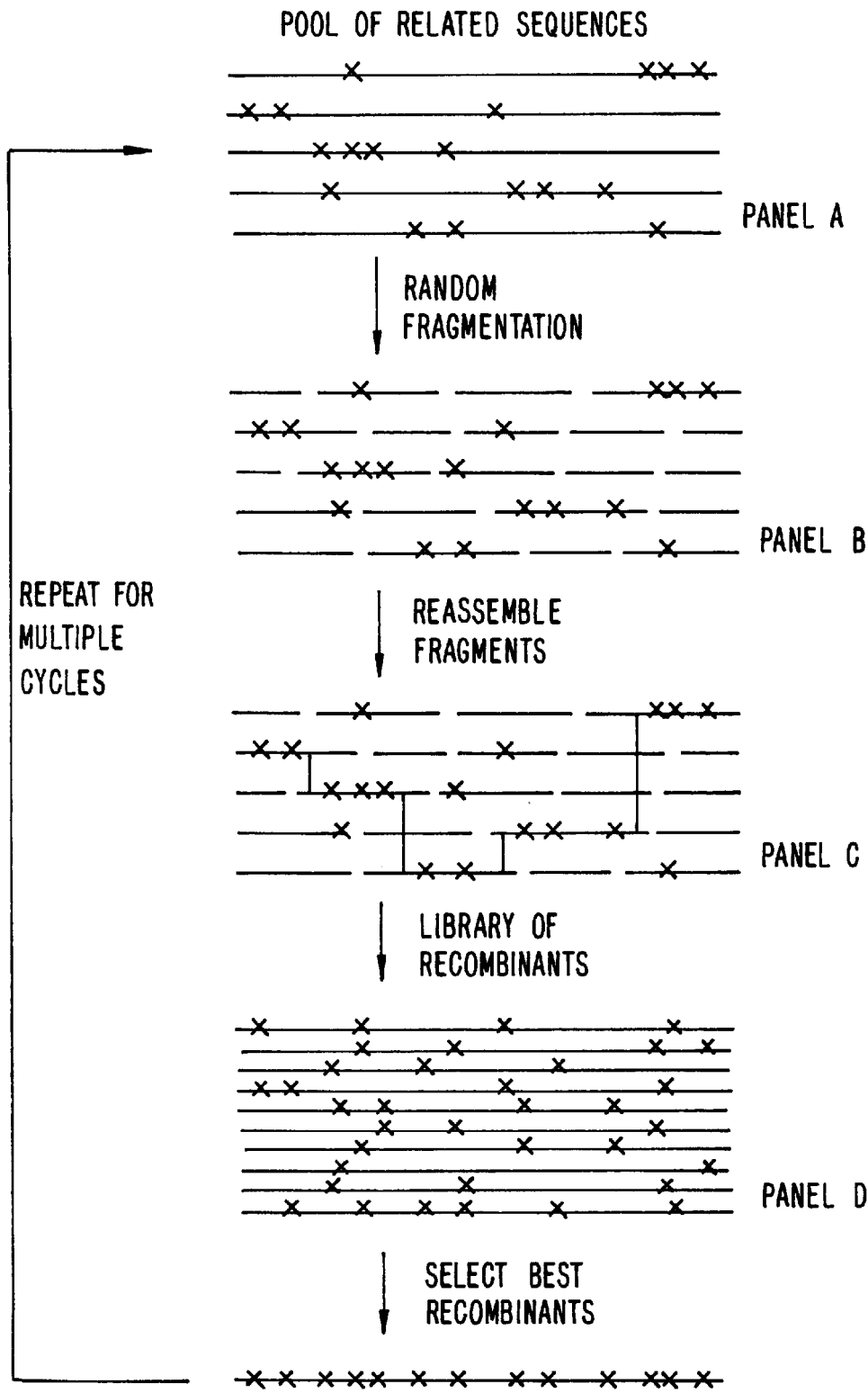
FIG. 1: Scheme for in vitro shuffling of genes.

Screening is, in general, a two-step process in which one first determines which cells do and do not express a screening marker and then physically separates the cells having the desired property. Selection is a form of screening in which identification and physical separation are achieved simultaneously by expression of a selection marker, which, in some genetic circumstances, allows cells expressing the marker to survive while other cells die (or vice versa). Screening markers include luciferase, β-galactosidase, and green fluorescent protein. Selection markers include drug and toxin resistance genes.

An exogenous DNA segment is one foreign (or heterologous) to the cell or homologous to the cell but in a position within the host cell nucleic acid in which the element is not ordinarily found. Exogenous DNA segments are expressed to yield exogenous polypeptides.

The term gene is used broadly to refer to any segment of DNA associated with a biological function. Thus, genes include coding sequences and/or the regulatory sequences required for their expression. Genes also include nonexpressed DNA segments that, for example, form recognition sequences for other proteins.

Percentage sequence identity is calculated by comparing two optimally aligned sequences over the window of comparison, determining the number of positions at which the identical nucleic acid base occurs in both sequences to yield the number of matched positions, dividing the number of matched positions by the total number of positions in the window of comparison. Optimal alignment of sequences for aligning a comparison window can be conducted by computerized implementations of algorithms GAP, BESTFIT, FASTA, and TFASTA in the Wisconsin Genetics Software Package Release 7.0, Genetics Computer Group, 575 Science Dr., Madison, Wis.

The term naturally-occurring is used to describe an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

DETAILED DISCLOSURE

I. General

The invention provides a number of strategies for transferring and/or evolving gene(s) associated with cellular DNA uptake such that they confer or enhance DNA-uptake capacity of recipient cells. One strategy entails evolving genes that confer competence in one species to confer either greater competence in that species, or comparable or greater competence in a second species. The second species expressing such as gene can then be transformed with DNA at high efficiency without the need for procedures such as chemical transformation or electroporation. Such genes can also be evolved to increase the efficiency of chemical transformation or electroporation. A second strategy entails evolving DNA segments that when present on incoming DNA increase the efficiency with which the incoming DNA is taken up. The evolved DNA segments are suitable for inclusion in standard cloning vectors. Cloning vectors incorporating such sequences are transformed at higher efficiency that would otherwise be the case, and/or can be transformed without the need to treat cells with chemicals or electroporation. A third strategy entails evolving viral receptors and/or viruses binding to the receptors to allow viruses to infect cells that would normally be resistant to viral infection. For example, the E. coli lamB receptor, which is recognized by phage lambda, can be transferred to different cell types, and evolved to allow lambda to infect such cell types. Optionally, lambda can itself be involved to increase the efficiency with which it infects the foreign cell type. A fourth strategy entails evolving genes conferring or associated with conjugative transfer for enhanced efficiency and/or efficicacy in a foreign cell type (donor or recipient).

The strategies generally entail evolution of gene(s) or segment(s) thereof to allow retention of function in a heterologous cell or improvement of function in a homologous cell. Evolution is effected by a process termed recursive sequence recombination, which can be achieved in many different formats and permutations of formats, as described in further detail below. These formats share some common principles. Recursive sequence recombination entails successive cycles of recombination to generate molecular diversity. That is, create a family of nucleic acid molecules showing substantial sequence identity to each other but differing in the presence of mutations. Each recombination cycle is followed by at least one cycle of screening or selection for molecules having a desired characteristic. The molecule(s) selected in one round form the starting materials for generating diversity in the next round. In any given cycle, recombination can occur in vivo or in vitro. Furthermore, diversity resulting from recombination can be augmented in any cycle by applying prior methods of mutagenesis (e.g., error-prone PCR or cassette mutagenesis) to either the substrates or products for recombination.

II. Formats for Recursive Sequence Recombination

Some formats and examples for recursive sequence recombination, sometimes referred to as DNA shuffling or molecular breeding, have been described by the present inventors and co-workers in copending application, attorney docket no. 16528A-014612, filed Mar. 25, 1996, PCT/US95/02126 filed Feb. 17, 1995 (published as WO 95/22625); Stemmer, *Science* 270, 1510 (1995); Stemmer et al., *Gene*, 164, 49–53 (1995); Stemmer, *Bio/Technology*, 13, 549–553 (1995); Stemmer, *Proc. Natl. Acad. Sci. USA* 91, 10747–10751 (1994); Stemmer, *Nature* 370, 389–391 (1994); Crameri et al., *Nature Medicine*, 2(1):1–3, (1996); Crameri et al., *Nature Biotechnology* 14, 315–319 (1996) (each of which is incorporated by reference in its entirety for all purposes).

(1) In Vitro Formats

One format for shuffling in vitro is illustrated in FIG. 1. The initial substrates for recombination are a pool of related sequences. The X's in the FIG. 1, panel A, show where the sequences diverge. The sequences can be DNA or RNA and can be of various lengths depending on the size of the gene or DNA fragment to be recombined or reassembled. Preferably the sequences are from 50 bp to 50 kb.

The pool of related substrates can be fragmented, usually at random, into fragments of from about 5 bp to 5 kb or more, as shown in FIG. 1, panel B. Preferably the size of the random fragments is from about 10 bp to 1000 bp, more preferably the size of the DNA fragments is from about 20 bp to 500 bp. The substrates can be digested by a number of different methods, such as DNAseI or RNAse digestion, random shearing or restriction enzyme digestion. The concentration of nucleic acid fragments of a particular length or sequence is often less than 0.1% or 1% by weight of the total nucleic acid. The number of different specific nucleic acid fragments in the mixture is usually at least about 100, 500 or 1000.

The mixed population of nucleic acid fragments are denatured by heating to about 80° C. to 100° C., more preferably from 90° C. to 96° C., to form single-stranded nucleic acid fragments and then reannealed. Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol ("PEG") or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%. The fragments that reanneal can be from different substrates as shown in FIG. 1, panel C.

The annealed nucleic acid fragments are incubated in the presence of a nucleic acid polymerase, such as Taq or Klenow, and dNTP's (i.e. dATP, dCTP, dGTP and dTTP). If regions of sequence identity are large, Taq polymerase can be used with an annealing temperature of between 45–65° C. If the areas of identity are small, Klenow polymerase can be used with an annealing temperature of between 20–30° C. The polymerase can be added to the random nucleic acid fragments prior to annealing, simultaneously with annealing or after annealing.

The cycle of denaturation, renaturation and incubation in the presence of polymerase is sometimes referred to as shuffling of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb, as shown in FIG. 1, panel D. The population represents variants of the starting substrates showing substantial sequence identity thereto but also diverging at several positions. The population has many more members than the starting substrates. The population of fragments resulting from shuffling is cloned into an appropriate vector and the ligation mixture used to transform host cells.

In a variation of in vitro shuffling, subsequences of recombination substrates can be generated by amplifying the full-length sequences under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering." In the subsequent amplification round, the incompletely extended products reanneal to and prime extension on different sequence-related template species.

In a further variation, at least one cycle of amplification can be conducted using a collection of overlapping single-stranded DNA fragments of related sequence, and different lengths. Each fragment can hybridize to and prime polynucleotide chain extension of a second fragment from the collection, thus forming sequence-recombined polynucleotides. In a further variation, ssDNA fragments of variable length can be generated from a single primer by Vent DNA polymerase on a first DNA template. The single stranded DNA fragments are used as primers for a second, Kunkel-type template, consisting of a uracil-containing circular ssDNA. This results in multiple substitutions of the first template into the second. See Levichkin et al., *Mol. Biology,* 29, 572–577 (1995).

(2) In Vivo Formats (a) Plasmid-Plasmid Recombination

The initial substrates for recombination are a collection of polynucleotides comprising variant forms of a gene. The variant forms usually show substantial sequence identity to each other sufficient to allow homologous recombination between substrates. The diversity between the polynucleotides can be natural (e.g., allelic or species variants), induced (e.g., error-prone PCR), or the result of in vitro recombination. Diversity can also result from resynthesizing genes encoding natural proteins with alternative codon usage. There should be at least sufficient diversity between substrates that recombination can generate more diverse products than there are starting materials. There must be at least two substrates differing in at least two positions. However, commonly a library of substrates of $10^3$–$10^8$ members is employed. The degree of diversity depends on the length of the substrate being recombined and the extent of the functional change to be evolved. Diversity at between 0.1–25% of positions is typical.

The diverse substrates are incorporated into plasmids. The plasmids are often standard cloning vectors, e.g., bacterial multicopy plasmids. However, in some methods to be described below, the plasmids include MOB functions. The substrates can be incorporated into the same or different plasmids. Often at least two different types of plasmid having different types of selection marker are used to allow selection for cells containing at least two types of vector. Also, where different types of plasmid are employed, the different plasmids can come from two distinct incompatibility groups to allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into cells by any transfection methods (e.g., chemical transformation, natural competence, electroporation or biolistics). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating the cells. However, cells that receive only one plasmid are unable to participate in recombination and the potential contribution of substrates on such plasmids to evolution is not fully exploited (although these plasmid may contribute to some extent if they are propagated in mutator cells). The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 $\mu$F and a 1–2 mM gap). Under these conditions, plasmids are exchanged between cells allowing all substrates to participate in recombination. In addition the products of recombination can undergo further rounds of recombination with each other or with the original substrate. The rate of evolution can also be increased by use of conjugative transfer. To exploit conjugative transfer, substrates can be cloned into plasmids having MOB genes, and tra genes are also provided in cis or in trans to the MOB genes. The effect of conjugative transfer is very similar to electroporation in that it allows plasmids to move between cells and allows recombination between any substrate, and the products of previous recombination to occur merely by propagating the culture. The details of how conjugative transfer is exploited in these vectors are discussed in more detail below. The rate of evolution can also be increased by fusing cells to induce exchange of plasmids or chrosomomes. Fusion can be induced by chemical agents, such as PEG, or viraL proteins, such as influenza virus hemagglutinin, HSV-1 gB and gD. The rate of evolution can also be increased by use of mutator host cells (e.g., Mut L, S, D, T, H and *Ataxia telangiectasia* human cell lines).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one would select for drug resistance. Cells surviving screening or selection can be subjected to one or more rounds of screening/selection followed by recombination or can be subjected directly to an additional round of recombination.

The next round of recombination can be achieved by several different formats independently of the previous round. For example, a further round of recombination can be effected simply by resuming the electroporation or conjugation-mediated intercellular transfer of plasmids described above. Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, and plasmid DNA from one subpopulation transfected into the other, where the substrates from the plasmids from the two subpopulations undergo a further round of recombination. In either of the latter two options, the rate of evolution can be increased by employing DNA extraction, electroporation, conjugation or mutator cells, as described above. In a still further variation, DNA from cells surviving screening/selection can be extracted and subjected to in vitro DNA shuffling.

After the second round of recombination, a second round of screening/selection is performed, preferably under conditions of increased stringency. If desired, further rounds of recombination and selection/screening can be performed using the same strategy as for the second round. With successive rounds of recombination and selection/screening, the surviving recombined substrates evolve toward acquisition of a desired phenotype. Typically, in this and other methods of recursive recombination, the final product of recombination that has acquired the desired phenotype differs from starting substrates at 0.1%–25% of positions and has evolved at a rate orders of magnitude in excess (e.g., by at least 10-fold, 100-fold, 1000-fold, or 10,000 fold) of the rate of naturally acquired mutation of about 1 mutation per $10^{-9}$ positions per generation (see Anderson & Hughes, *Proc. Natl. Acad. Sci. USA* 93, 906–907 (1996)).

(b) Virus-Plasmid Recombination

The strategy used for plasmid-plasmid recombination can also be used for virus-plasmid recombination; usually, phage-plasmid recombination. However, some additional comments particular to the use of viruses are appropriate. The initial substrates for recombination are cloned into both plasmid and viral vectors. It is usually not critical which substrate(s) are inserted into the viral vector and which into the plasmid, although usually the viral vector should contain different substrate(s) from the plasmid. As before, the plasmid (and the virus) typically contains a selective marker. The plasmid and viral vectors can both be introduced into cells by transfection as described above. However, a more efficient procedure is to transfect the cells with plasmid, select transfectants and infect the transfectants with virus. Because the efficiency of infection of many viruses approaches 100% of cells, most cells transfected and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination. Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions. Other viruses, such as the T-phage and lytic lambda, undergo recombination with the plasmid but ultimately kill the host cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny phage can be used to transfect or infect cells surviving a previous round of screening/selection, or fresh cells transfected with fresh substrates for recombination.

(c) Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates. Preferably, the virus is one that, naturally or as a result of mutation, does not kill cells. After insertion, some viral genomes can be packaged in vitro. The packaged viruses are used to infect cells at high multiplicity such that there is a high probability that a cell will receive multiple viruses bearing different substrates.

After the initial round of infection, subsequent steps depend on the nature of infection as discussed in the previous section. For example, if the viruses have phagemid genomes such as lambda cosmids or M13, F1 or Fd phagemids, the phagemids behave as plasmids within the cell and undergo recombination simply by propagating the cells. Recombination is particularly efficient between single-stranded forms of intracellular DNA. Recombination can be augmented by electroporation of cells. Following selection/screening, cosmids containing recombinant genes can be recovered from surviving cells (e.g., by heat induction of a cos⁻ lysogenic host cell), repackaged in vitro, and used to infect fresh cells at high multiplicity for a further round of recombination.

If the viruses are filamentous phage, recombination of replicating form DNA occurs by propagating the culture of infected cells. Selection/screening identifies colonies of cells containing viral vectors having recombinant genes with improved properties, together with phage extruded from such cells. Subsequent options are essentially the same as for plasmid-viral recombination.

(d) Chromosome-Plasmid Recombination

This format can be used to evolve both the chromosomal and plasmid-borne substrates. The format is particularly useful in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation or electroporation. Evolution can be further accelerated by use of mutator host cells or by seeding a culture of nonmutator host cells being evolved with mutator host cells and inducing intercellular transfer of plasmids by electroporation or conjugation. Preferably, mutator host cells used for seeding contain a negative selection marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid—plasmid recombination. For example, further recombination can be effected by propagating cells surviving recombination in combination with electroporation or conjugative transfer of plasmids. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

(e) Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

III. Evolution and/or Transfer of Genes Conferring Cellular Uptake Capacity (1) Genes Conferring Cellular Uptake Capacity The strategy of this approach is to take a gene (for example, a coding sequence or a cis-acting nonexpressed sequence) associated with DNA uptake capacity in one cell type, and to evolve that gene either for improved DNA uptake capacity in the same cell type or so that it can function in a second cell type. A gene is associated with DNA uptake capacity if, in at least some circumstances, cells bearing a functional copy of the gene take up DNA more effectively than cells lacking such a copy. Efficacy can be determined, for example, either by the percentage of cells taking up DNA (i.e., competence) or by the ratio of transformed cells to mass input DNA (transfection efficiency). Genes of particular interest are those associated with natural competence. That is, genes that allow bacterial or eucaryotic cells to take up DNA from the media without elaborate preparatory steps, such as in chemical transformation or electroporation. Some such genes were discussed in the background section. In nature, natural competence is most efficient when cells are starved for a carbon source. However, by evolution and/or high-level recombinant expression of genes conferring competence, cells harboring such genes can take up DNA directly from culture media, with few, if any, preparatory steps. Genes that confer high transfection efficacy as a result of some preparatory treatment of cells are also of interest.

In some instances, the starting material for recursive recombination is a discrete gene or cluster of genes known to be associated with DNA-uptake capacity. The starting material can also be a segment of such a gene or cluster, that is recombined in isolation of its surrounding DNA, but is relinked to its surrounding DNA before screening/selection of recombination products. In other instances, the starting material for recombination is a larger segment of DNA that includes a coding sequence or other locus associated with DNA-uptake at an unknown location. For example, the starting material can be a chromosome, episome, BAC or YAC clones. In still other instances, the starting material is the whole genome of an organism that is known to have desirable DNA-uptake characteristics, but for which no information localizing the genes associated with these characteristics is available.

(2) Recipient Cells

In general any type of cells for which improved DNA-uptake properties are desired can be used as a recipient of evolved genes. Cells of particular interest include eukaryot cells, particularly mammalian cells (e.g., mouse, hamster, primate, human), both cell lines and primary cultures. Such cells include stem cells, including embryonic stem cells, zygotes, fibroblasts, lymphocytes, Chinese hamster ovary (CHO), mouse fibroblasts (NIH3T3), kidney, liver, muscle, and skin cells. Other eucaryotic cells of interest include plant cells, such as maize, rice, wheat, cotton, soybean, sugarcane, tobacco, and arabidopsis; fish, algae, fungi (*aspergillus, podospora, neurospora*), insect (e.g., *baculo lepidoptera*), yeast (*picchia and saccharomyces*). Also of interest are many bacterial cell types, both gram-negative and gram-positive, such as Bacillus, *Escherichia coli*, Pseudomonas, Salmonella, and Erwinia.

(3) Application of Recursive Recombination Formats to Evolving Genes Conferring DNA Uptake Capacity in a Recipient Cell The procedure starts with at least two substrates, which generally show substantial sequence identity to each other (i.e., at least about 50%, 70%, 80% or 90% sequence identity) but differ from each other at certain positions. The difference can be any type of mutation, for example, substitutions, insertions and deletions. Often, different segments differ from each other in perhaps 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second as a single position, and the second can differ from the third at a different single position. The starting DNA segments can be natural variants of each other, for example, allelic or species; variants. The segments can also be from nonallelic genes showing some degree of structural and usually functional relatedness (e.g., different genes within a superfamily such as the immunoglobulin superfamily). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the formats described above to generate a diverse library of recombinant DNA segments. Such a library can vary widely in size from having fewer than 10 to more than $10^5$, $10^7$, or $10^9$ members. In general, the starting segments and the recombinant libraries generated include full-length coding sequences and any essential regulatory sequences, such as a promoter and polyadenylation sequence, required for expression. However, if this is not the case, the recombinant DNA segments in the library can be inserted into a common vector providing the missing sequences before performing screening/selection.

If the recursive recombination format employed was an in vivo format, the library of recombinant DNA segments generated already exists in a cell, which is usually, the cell type in which enhanced DNA-uptake characteristics are desired. If recursive recombination was performed in vitro, the recombinant library should be introduced into the desired cell type before screening/selection. The members of the recombinant library can be linked to an episome before introduction or can be introduced directly. The manner in which the library is introduced into the cell type depends on the original DNA-uptake characteristics of the cell type. For example, if the cell type is insusceptible to natural and chemical-induced competence, but susceptible to electroporation, one would usually employ electroporation. If the cell type is insusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells. The process is applicable to a wide range of tissues, including plants, bacteria, fungi, algae, intact animal tissues, tissue culture cells, and animal embryos. Alternatively, one can employ electronic pulse delivery, which is essentially a mild electroporation format for live tissues in animals and patients. Zhao, *Advanced Drug Delivery Reviews* 17, 257–262 (1995). After introduction of the library of recombinant DNA genes, the cells are optionally propagated to allow expression of genes to occur.

Figure 2:
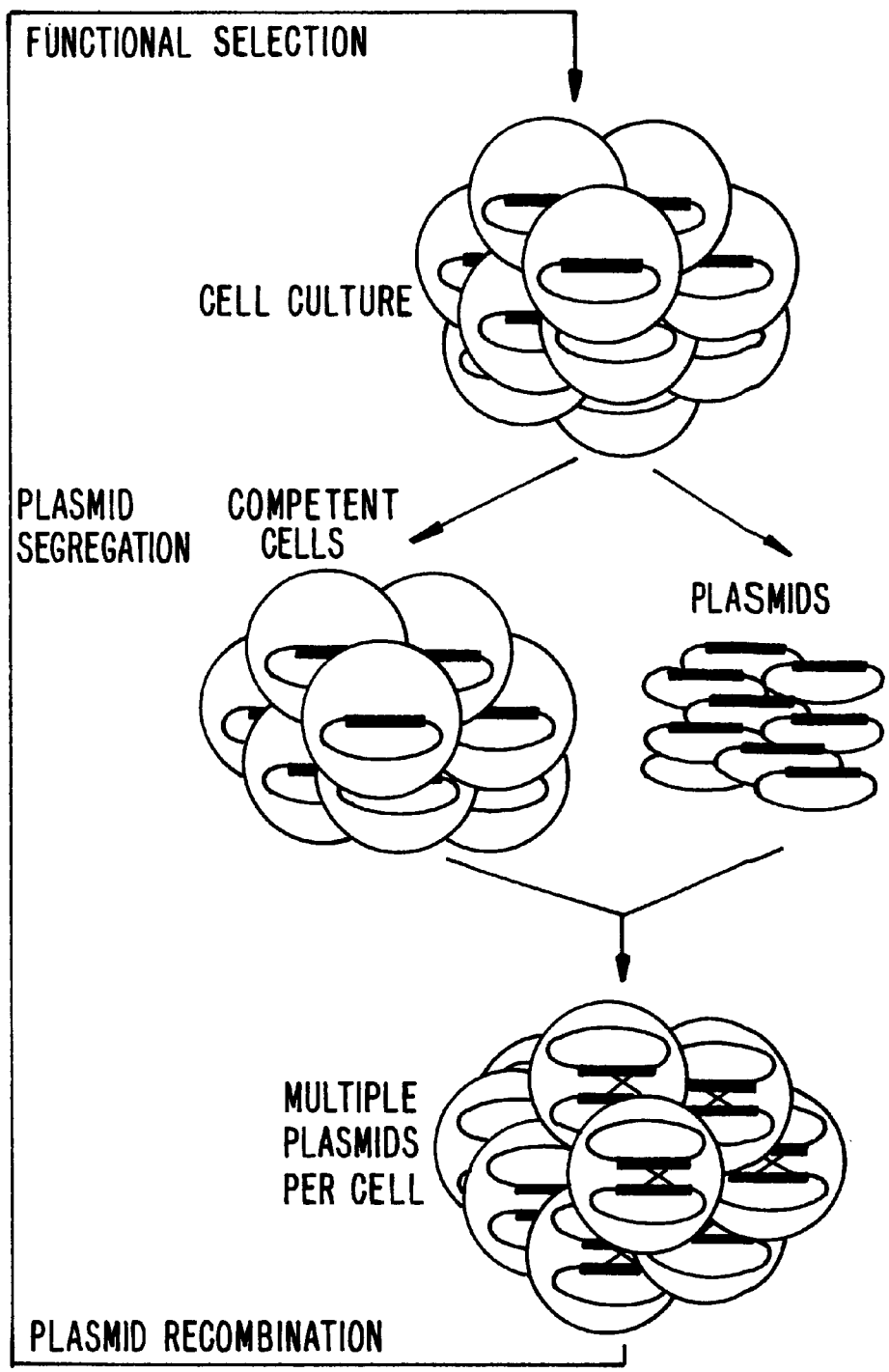
FIG. 2: Scheme for selecting genes conferring competence.

The goal of screening/selection is to identify members of the library of recombinant genes conferring enhanced DNA-uptake characteristics in the recipient cell. Screening/selection is usually performed by introducing a vector bearing a marker into the recipient cells transformed with the recombinant library, and screening or selecting for cells expressing the marker, as shown in FIG. 2. Alternatively, the vector bearing the marker can be co-introduced with the recombinant library.

The upper part of FIG. 2 represents a collection of cells containing a library of variant competence genes differing between different cells. The collection of cells is then transfected with a vector encoding a marker function in the cells. The conditions under which the vector bearing the marker is introduced into the cells should be the conditions under which one wants to evolve the uptake genes to confer improved performance. That is, if a gene is evolved to confer natural competence, the vector should be introduced into the cells under a natural competence regime. The natural competence regime can be increased in stringency in successive rounds of screening/selection. For example, one can start with a regime in which cells have been starved of a carbon source, and progress to a regime in which DNA is simply added to a nutrient-rich broth. If a gene is to be evolved to confer enhanced electroporation characteristics, the vector should be introduced into the cells by electroporation. If the gene is to be evolved to confer enhanced chemical transformation, the vector should be introduced into the cells by chemical transformation. The marker should be capable of being expressed and readily detected in the recipient cell type, but its characteristics are not otherwise critical. For examples, genes conferring drug resistance, such as $neo^R$, $Cm^R$, $Ap^R$, $Kn^R$, Hyg, $His^D$, Gpt, Ble, Hprt, HSV-tk, Gpt, Diphtheria toxin, ricin toxin, and cytosine deaminase are suitable.

In some embodiments, the vector bearing the marker is a suicide vector. That is, a vector that transiently expresses the marker for a sufficient time to screen for or select a cell bearing the vector, but which is then degraded or otherwise rendered incapable of expressing the marker. The advantage of using a suicide vector is that subsequent rounds of screening/selection (to be described below) can be employed using the same marker. For example, some suicide vectors express a long-lived toxin which is neutralized by a short-lived molecule expressed from the same vector. Expression of the toxin alone will not allow vector to be established. Jense & Gerdes, *Mol. Microbiol.*, 17, 205–210 (1995); Bernard et al., *Gene* 162, 159–160. Alternatively, a vector can be rendered suicidal by incorporation of a defective origin of replication or by omission of an origin of replication. Such vectors can be selected to have a wide range of stabilities.

The pool of cells surviving screening/selection is enriched for recombinant genes conferring enhanced DNA-uptake capacity (see FIG. 2). Further enrichment can be obtained, if desired, by performing a second round of screening/selection without generating additional diversity. If a suicide vector was employed in the initial screening/selection, the same vector can be employed in the second round. Otherwise, a vector bearing a different marker and having a different compatibility origin is required. Cells surviving two rounds of screening/selection are further enriched for a recombinant gene or pool of such genes conferring enhanced uptake characteristics.

The recombinant gene or pool of such genes surviving one round of screening/selection forms one or more of the substrates for a second round of recombination. Again recombination can be performed in vivo or in vitro by any of the recursive recombination formats described above. If recursive recombination is performed in vitro, the recombinant gene or genes to form the substrate for recombination should be extracted (or PCR amplified) from the cells in which screening/selection was performed. Optionally, a subsequence of such gene or genes can be excised for more targeted subsequent recombination. If the recombinant genes are contained within episomes, their isolation presents no difficulties. If the recombinant genes are chromosomally integrated, they can be isolated by amplification primed from known sequences flanking the regions in which recombination has occurred. Alternatively, whole genomic DNA can be isolated, optionally amplified, and used as the substrate for recombination. Small samples of genomic DNA can be amplified by whole genome amplification with degenerate primers (Barrett et al., *Nucleic Acids Research* 23, 3488–3492 (1995)). These primers result in a large amount of random 3' ends, which can undergo homologous recombination when reintroduced into cells.

Figure 3:
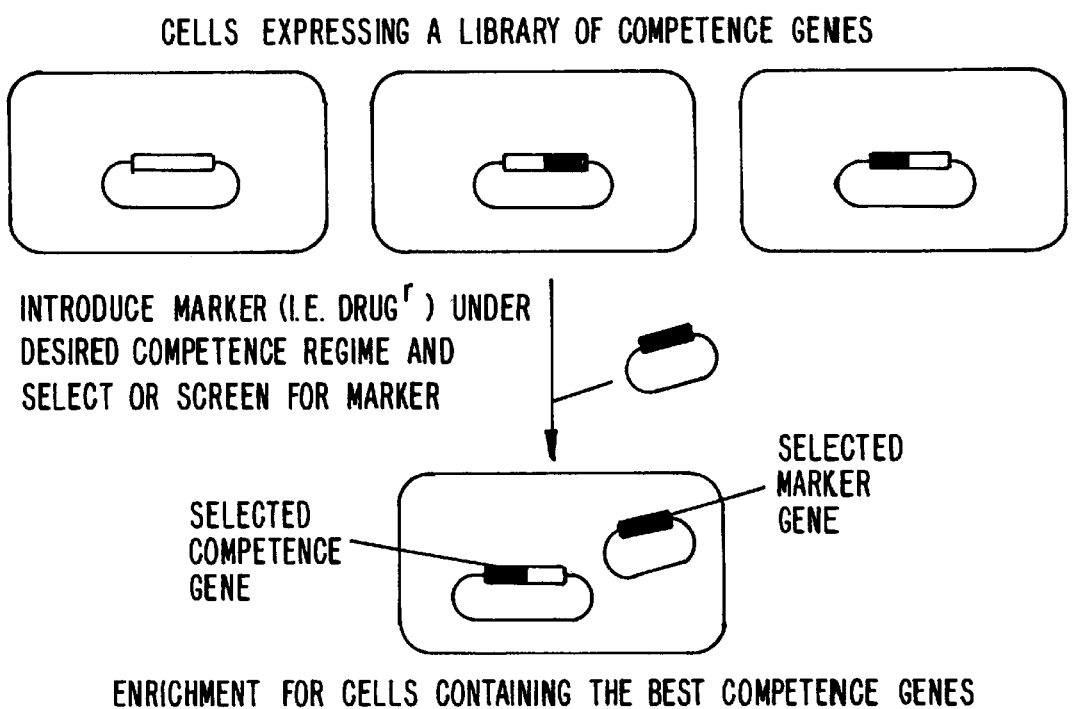
FIG. 3: Scheme for performing recombination between recombinant genes surviving a previous round of screening/selection.

If the second round of recombination is to be performed in vivo, as is often the case, it can be performed in the cell surviving screening/selection, or the recombinant genes can be transferred to another cell type (e.g., a cell type having a high frequency of mutation and/or recombination). In this situation, recombination can be effected by introducing additional DNA segment(s) into cells bearing the recombinant genes. In other methods, the cells can be induced to exchange genetic information with each other by, for example, electroporation. In some methods, the second round of recombination is performed by dividing a pool of cells surviving screening/selection in the first round into two subpopulations (see FIG. 3). DNA from one subpopulation is isolated and transfected into the other population, where the recombinant gene(s) from the two subpopulations recombine to form a further library of recombinant genes. In these methods, it is not necessary to isolate particular genes from the first subpopulation or to take steps to avoid random shearing of DNA during extraction. Rather, the whole genome of DNA sheared or otherwise cleaved into manageable size fragments is transfected into the second subpopulation. This approach is particularly useful when several genes are being evolved simultaneously and/or the location and identity of such genes within chromosome are not known.

The second round of recombination is sometimes performed exclusively among the recombinant molecules surviving selection. However, in other embodiments, additional substrates can be introduced. The additional substrates can be of the same form as the substrates used in the first round of recombination. That is, additional natural or induced mutants of the gene or cluster of genes, forming the substrates for the first round. Alternatively, the additional substrate(s) in the second round of recombination can be exactly the same as the substrate(s) in the first round of replication. Inclusion of a substrate representing a wildtype version of the gene or genes being evolved (i.e., a backcross) is useful to reduce the occurrence of neutral mutations (i.e., mutations that represent a sequence variation from a wildtype sequence but do not confer any useful DNA-uptake characteristics).

After the second round of recombination, recombinant genes conferring enhanced DNA-uptake are again selected. The selection process proceeds essentially as before. If a suicide vector bearing a selective marker was used in the first round of selection, the same vector can be used again. If the vector used in the first round of selection was not a suicide vector, and the same cells are being used for the first and second rounds of selection (as would usually happen if the second round of recombination is performed in vivo), the vector used in the second round of selection should have a second selective marker different from the first selective marker and preferably, an original of replication compatible with coexistence with the vector bearing the first selective marker. Again, a cell or pool of cells surviving selection is selected. If a pool of cells, the cells can be subject to further enrichment for desired recombinants before any subsequent rounds of recombination. Optionally, cultures of cells can be propagated from individual colonies surviving selection and the cultures quantitatively compared for transfection efficacy (which may be determined by transfection capacity, transfection efficiency or % cells taking up DNA).

Subsequent rounds of recombination and screening/selection follow the same principles as the second round. The products of any round of selection/screening form at least one of the substrates for the next round of recombination. Each round of screening/selection can generate a pool of recombinants enriched for enhanced DNA uptake capacity, and subsequent rounds of recombination generate further diversity from the best recombinant sequences from a previous round. The stringency of selection can be increased at each round by decreasing the amount and/or concentration of vector bearing the selective marker. Eventually, cells surviving selection contain recombinant gene or genes conferring acceptable DNA-uptake characteristics. Ideally, such cells have a high degree of natural competence. That is, a significant proportion or cells (from about $10^{-7}$ to 1) in a culture take up DNA on contact without chemical treatment or electroporation. Such cells also achieve substantial transfection efficiencies of about $10^3$ to $10^{10}$ colonies per $\mu g$ of DNA. Depending in part on the cell type growth characteristics, several rounds of recombination and selection can be performed in only a few weeks, resulting in 10-, 100- or 1000-fold improvement in DNA uptake characteristics.

IV. Evolution of DNA Sequences to Enhance Uptake in a Vector

The invention further provides methods of enhancing DNA sequences suitable for inclusion on a vector that increase the efficiency with which that vector can be taken up or established by recipient cells (bacterial or eucaryotic) of interest. Such DNA sequences can have roles in transfer, integration, stability or expression of the vector containing them. Vectors including DNA-uptake enhancing sequences, can, if desired, be used for transfection of cells bearing the modified genes discussed above. The starting substrates for evolving DNA sequences in the present methods can be from natural DNA sequences known or suspected to have a role in enhancing DNA uptake. Some examples of such sequences were discussed in the Background section. Such sequences can be from the same or different organism as the recipient cell type into which transfection of vectors bearing evolved sequences is contemplated. The starting substrates can also be theoretical or even random sequences not known to enhance vector uptake. For example, one of the starting substrates can simply be a standard cloning vector without an exogenous insert. Whatever sequences within the vector are closest to being a vector-uptake enhancing sequence evolve to fulfill this role.

As was the case in evolving sequences for incorporation into recipient cells, the substrates in the present methods differ in at least two nucleotides, such that increased diversity can be generated by recombination of two substrates. As previously discussed, the variation between the substrates can be the result of selection of allelic or species variant sequences, nonallelic but related sequences, or induced mutations.

The recursive recombination in the present methods follows the same pattern of recursive cycles of recombination and screening/selection described above. If a cycle of recombination is performed in vitro, the DNA segment being evolved may or may not be present as part of a vector having a marker sequence. If the DNA segment is evolved in isolation of a vector, the library of recombinant DNA segments resulting from recombination are inserted into a vector including a marker sequence capable of being expressed in the intended recipient cell type before the next screening/selection step. If a cycle of recombination is performed in vivo, the products of recombination should isolated and, if not already part of a vector suitable for screening/selection, inserted into such a vector.

Figure 4:
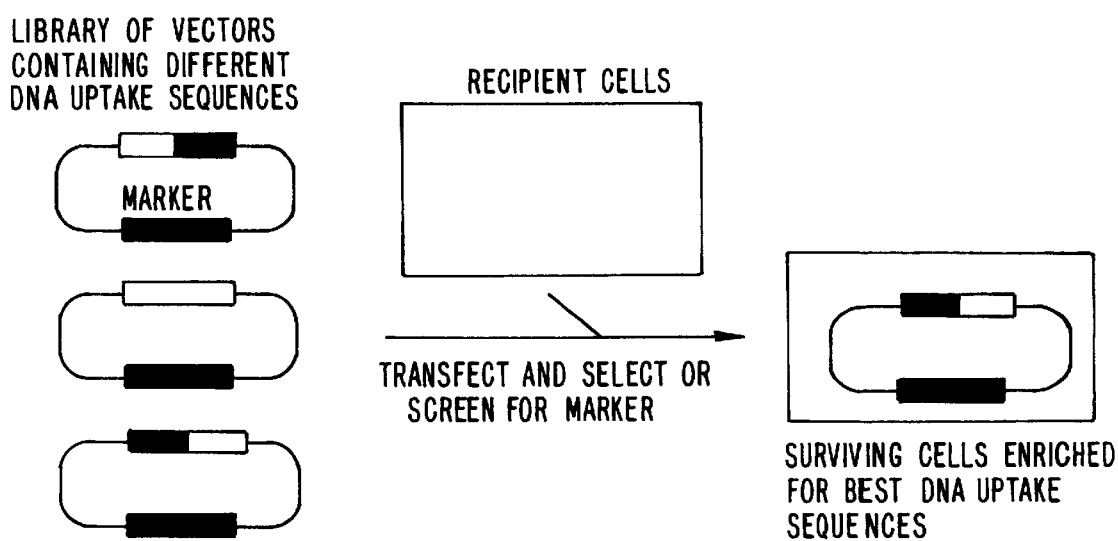
FIG. 4: Scheme for selecting DNA sequences enhancing DNA uptake when present on a vector.

Screening/selection is effected by introducing a library of recombinant vectors bearing different recombined DNA segments and a marker sequence into recipient cells of interest and screening or selecting a subpopulation of cells expressing the marker (see FIG. 4). The conditions in which the library of vectors is introduced into cells should be those in which it is contemplated that vectors incorporating the DNA segment being evolved will subsequently be used. For example, if it is intended to evolve a DNA segment for use in vectors taken up by natural competence, the library of recombinant vectors should be introduced into cells by a natural competence regime. If the evolved DNA segment is intended for use in vectors taken up electroporation, the recombinant vectors should be introduced into cells by electroporation.

The subpopulation of cells expressing the marker sequence are enriched for vectors bearing recombinant segments enhancing the transfection efficiency of the vector. If desired, vector DNA can be reisolated from this subpopulation of cells and transfected into further cells. Cells surviving two rounds of selection/screening are further enriched for recombinant segments having the best DNA-uptake enhancing properties. If desired, individual recombinant vectors can be isolated and quantitatively compared for transfection efficiency. Because in the present methods, it is a vector sequence rather than a recipient cell that is being evolved, vectors can be transfected into fresh cells in each round of screening/selection. Thus, in general, there is no need to use suicide vectors or different markers in each round of screening/selection.

Subsequent rounds of recombination can be performed in vivo or in vitro. As discussed above, at least one substrate for subsequent rounds of recombination is the product(s) of a previous round. The other substrate can also be product(s) or previous round, one of the starting substrates, a different substrate. If in vitro, DNA is isolated from the cells surviving screening/selection, usually as an episome or amplified PCR fragment, before recombination. If recombination is performed in vivo, it can be performed either in the subpopulation of cells surviving screening/selection or DNA can be isolated from these cells and transferred to other cells. In either situation, the recombinant DNA segments generated by recombination are isolated from the cells in which recombination occurred before performing the next round of selection/screening. Subsequent rounds of selection/screening are generally performed in fresh recipient cells and present no particular difficulties. Stringency of selection/screening can be increased in successive rounds by, for example, decreasing the ratio of recipient cells to transfected DNA. Alternatively, the conditions can be made less conducive to transfection in successive rounds, e.g., by changing the transfection buffer or decreasing the time with which DNA is contacted with cells.

After several rounds of recombination and selection/screening, at least one of the surviving recombinant DNA vectors contains a segment conferring the desired transfection characteristics. For example, recipient cells of interest take up the vector with a transfection efficiency of about $10^{-9}, 10^{-7}, 10^{-5}, 10^{-3}, 10^{-1}$ or 1 transfectants per input DNA molecule. If DNA segments have been recombined in isolated form (i.e., free of other vector sequences), the sequence conferring enhanced DNA uptake is readily localized to a specific region of a vector, and can be excised and transferred to other vectors by standard methods. These vectors can then be used in standard cloning procedures to achieve higher transfection efficiencies. Alternatively, and depending on the recipient cell for which the DNA sequence was evolved, vectors bearing evolved sequences can be transfected into cell types not hitherto commonly used in genetic engineering.

V. Evolution of Viral Receptors

The invention further provides methods for transferring and/or evolving viral receptors, and cells bearing heterologous and/or modified viral receptors generated by such methods. Cells that are usually completely or substantially insusceptible to infection by a virus can be rendered susceptible to infection by expression of a heterologous or modified viral receptor on their surface and/or by evolution of other cellular genes needed to support viral infection.

Receptors of greatest interest for evolution are those recognized by viruses commonly used in genetic engineering for which in vitro packaging systems are available or can be devised. The most well known such virus is phage lambda. Lambda DNA vectors bearing inserts can be packaged at high efficiency (e.g., up to about $10^9$ pfu/$\mu$g) using commercially available packaging extracts. Other phage for which in vitro packaging systems have been reported include T3, Fujisawa et al., *Virology* 101, 327–334 (1978); T7, Masker et al. *J. Virol.* 27, 149–163 (1978); P22, Strobel et al., 1984; and T1, Liebeschuetz et al., *Mol. Gen. Genet.* 200, 451–457 (1985). Additional receptors of interest are those recognized by viruses useful for transduction, such as P1 and T4.

Known viral receptors include lamB (recognized by phage lambda); the *E. coli* sex pilus, recognized by M13 (and other filamentous phage); and CD4, recognized by HIV. Other pairs of virus and known or suspected receptor(s) include: polio, Immunoglobulin superfamily protein; rhinovirus, ICAM-1; semliki forest, H-2 antigens; lactate dehydrogenase, or 1a antigens; rabies, acetylcholine receptor; vesicular stomatitis, phosphatidylserine; influenza $A^a$, sialic acid; reovirus serotype 3, $\beta$-adrenergic receptor; Epstein-Barr, complement receptor 2 (CR2); vaccinia, epidermal growth factor receptor; hepatitis B, IgA receptor; measles virus, substance P, *Cell Mol. Neurobiol.* 12, 397–409 (1992); human cytomegalovirus, phosphorylated glycoprotein, *J. Virol.* 66, 4834–8 (1992); coxsackie B viruses, 100-kDa binding protein, *J. Virol.* 69, 6751–7 (1995); measles virus haemagglutinin, CD48, *J. Gen. Virol.* 76, 2793–800 (1995); human coronavirus 229E, human aminopeptidase N, *Nature* 357, 420–2 (1992); sindbis virus, laminin receptor, *J. Virol.* 66, 4992–5001 (1992).

Cell types of interest to serve as recipients of heterologous/evolved viral receptors are in general the same as the cell types listed as recipients for evolution of genes conferring competence (see Section III). Of particular interest are bacterial cells other than *E. coli*, such as Bacillus and Streptomyces, yeast, and mammalian cells.

Often the initial substrates for recombination are from a single gene encoding the viral receptor of interest. For heteromultimeric receptors, genes encoding each subunit can be evolved simultaneously. The substrates can be variants of an intact gene or a subsequence thereof. As in other methods, the variation between the starting substrates for recombination can be the result of natural processes or induced. For viral receptors occurring only in a single cell type (e.g., lamB in *E. coli*), there is little available natural diversity, so the variation between the initial substrates is typically induced (e.g., by error-prone PCR, insertion of a mutation cassette or passage through a mutator strain). The initial substrates (and substrates in subsequent rounds of replication) can include additional DNA segments that contain genes of known or unknown function that are also required or facilitate introduction, establishment and/or productive infection of a virus in a recipient cell. It is not necessary that one know the location of such genes. For example, the substrates can include a full chromosome or genome of the cell to be rendered susceptible to viral infection.

If recombination is performed in vitro, the products of recombination are optionally linked to an expression vector, if they are not already so linked, and introduced into the cells to be rendered susceptible to viral infection. The manner of introduction (e.g., whether by chemical transformation, or electroporation) is not critical. If recombination is performed in vivo, it is usually performed in the cell type to be rendered susceptible to viral infection, and so no comparable step of introducing DNA is required. Irrespective how generated, populations of cells harboring recombinant genes are usually propagated to allow expression of the genes before the selection/screening step.

The manner of selection/screening depends on the ultimate goal in rendering a cell susceptible to viral infection. For most genetic engineering purposes, it is sufficient and often preferable, that viral infection proceeds to allow replication of the viral genome and/or expression of any exogenous genes on the genome, but does not produce infectious viral particles and/or kill the host cell. If stable expression is the goal, screening/selection can be achieved by incorporating a marker sequence in the viral genome. Markers of the kind discussed in section III are equally suitable here. For example, FIG. 5A shows a virus encoding a marker being contacted with a collection of cells harboring a library of variant receptor genes (on a vector) and a library of variant forms of other genes associated with viral infection (chromosomally located). Cells expressing a receptor recognized by the virus and having other genes appropriate to support viral infection are infected with virus and the subpopulation of cells expressing the marker are screened or selected. As in the methods for evolving cellular competence genes (Section III), it is often preferable that the same screening/selection marker can be used in multiple rounds of selection/screening. This can be achieved by infecting recipient cells with suicidal virus analogous to the suicidal vectors previously discussed. That is, a suicidal virus can encode a combination of a long-lived toxin and a short-lived molecule which neutralizes the toxin (see Jense & Gerdes, supra).

Figure 5A:
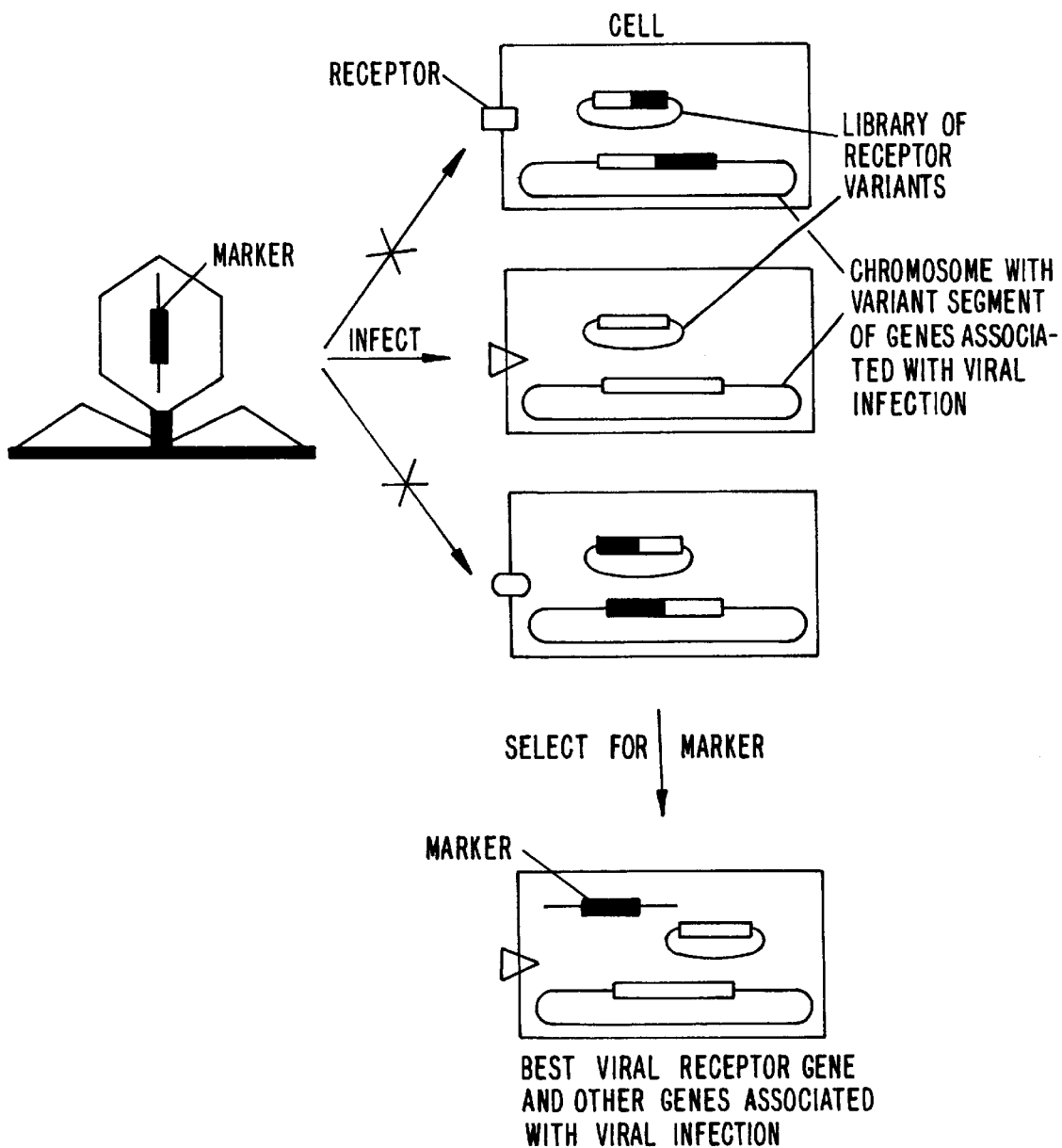
FIGS. 5A and 5B: Schemes for selecting viral receptor genes and other cellular genes conferring susceptibility to viral infection.
Figure 5B:
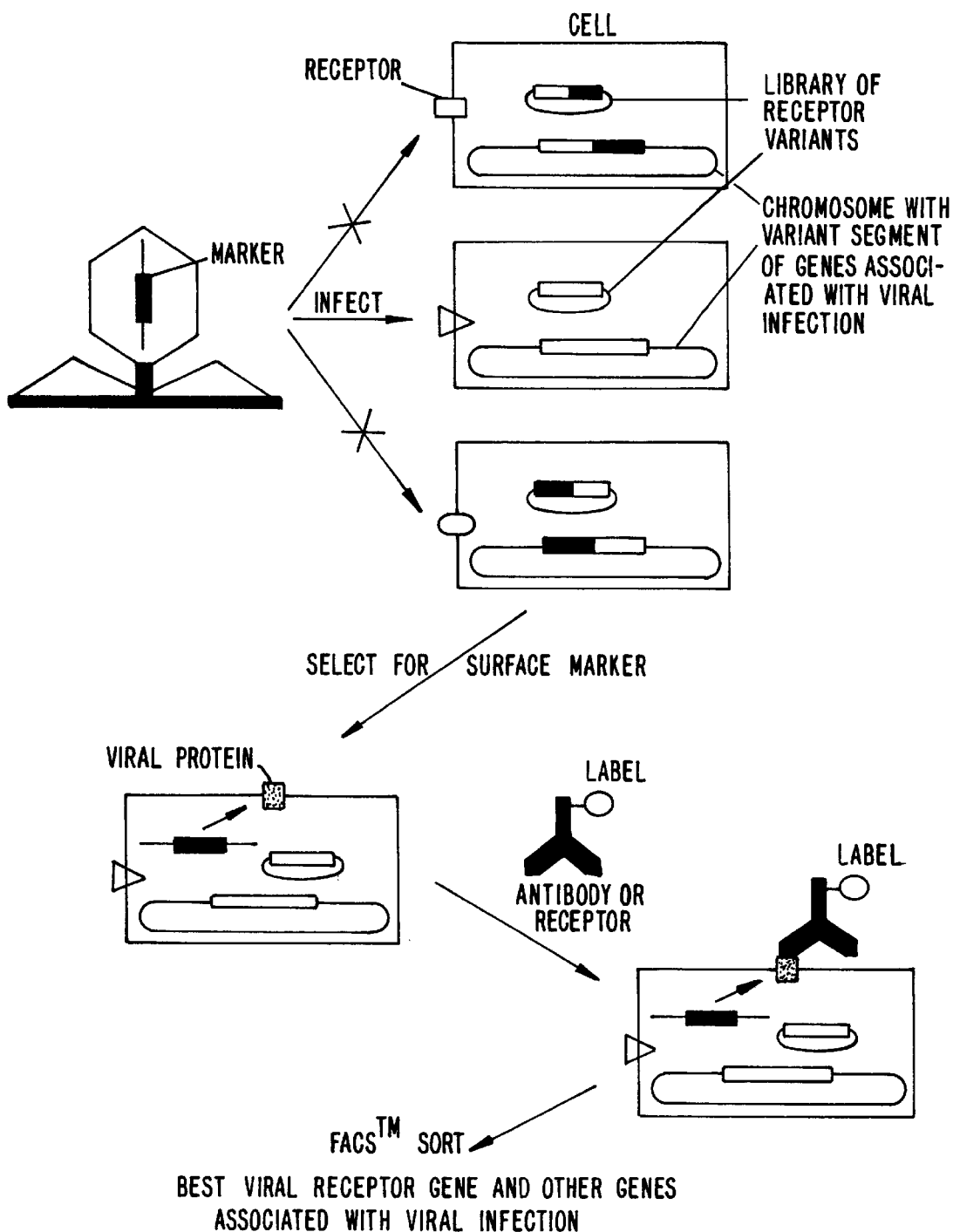
Figure 6A:
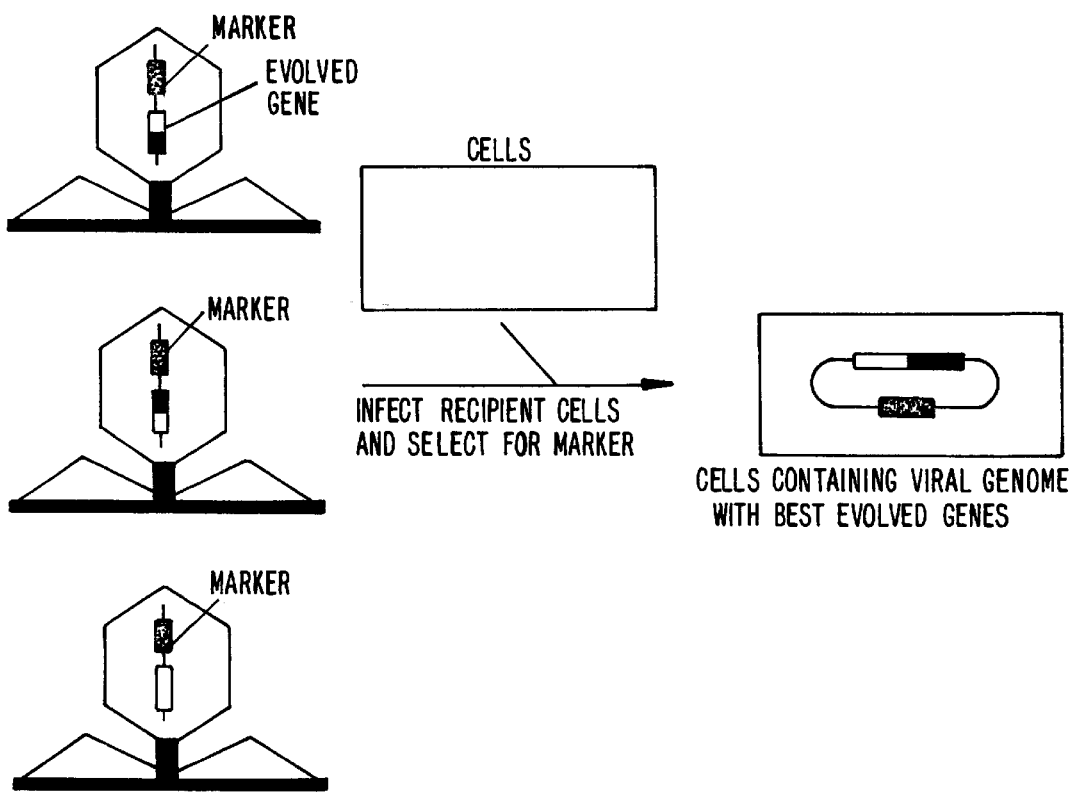
FIGS. 6A and 6B: Selection for viruses capable of infecting a cell.
Figure 6B:
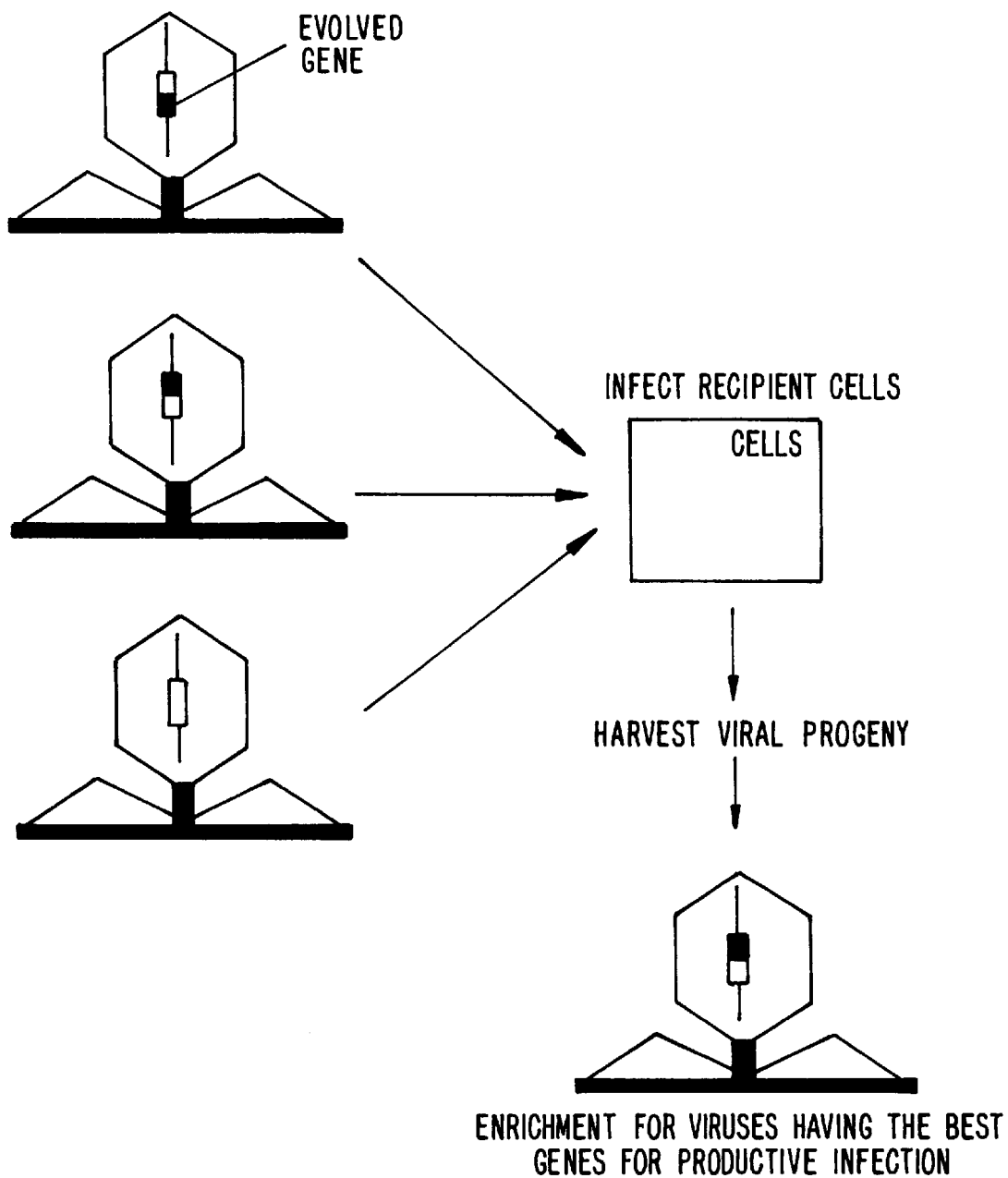

If the goal is to achieve recipient cells susceptible to productive viral infection, a different manner of screening/ selection is required. One approach is to FACS™-sort for necrotic cells, which take up stain differently than viable cells. Alternatively, one can FACS™-sort for a viral (or marker) protein expressed on the outersurface of cells using a labelled target (e.g., an antibody) having specific affinity for the viral protein (see FIG. 5B). In still other methods, a viral gene encoding a function associated with productive viral infection is replaced with a marker sequence and one screens/selects for expression of the marker sequence. For example, many viruses encode a gene that degrades host cellular DNA. If expressed, this gene would usually kill the host cell. By replacing the gene with a marker, expression of the marker serves to indicate that the cell is capable of expressing the lethal gene; nevertheless the cell survives thereby preserving the genetic materials that confer susceptibility to productive viral infection. The cells surviving screening/selection by any of these methods encode a viral receptor evolved to permit infection and/or other genes needed for the virus to productively infect the cells.

Subsequent steps in evolution of the viral receptor and/or other cellular genes that support viral infection proceeds in a closely analogous fashion to that described for evolving cellular competence genes. For example, further round(s) of selection/screening can be performed before performing the next recombination step. The next recombination step can be performed in vitro by isolating DNA from cells used in selection. Alternatively, further substrate(s) for recombination can be introduced into the cells surviving selection for a round of in vivo recombination. A particularly effective strategy for evolution of a viral receptor together with cellular genes of unknown location that support viral infection is one of dividing cells surviving a previous round of screening/selection in two pools. Total DNA is extracted from one pool and introduced into the other pool, where it recombines with endogenous DNA. Thus, the best recombinant DNA segments from a previous round of screening/ selection are allowed to recombine with each other. Stringency can be increased in successive rounds of screening/ selection by e.g., decreasing the time for which the virus is contacted with recipient cells.

The goal of evolving viral receptors and/or ancillary cellular genes is achieved when recipient cells can be infected with virus at a desired efficiency. In some applications, efficiency is not critical and it is sufficient that a cell that was previously substantially or completely insusceptible to viral infection is rendered at least somewhat susceptible to infection. In other application, such as generation of primary recombinant libraries in cloning procedures, efficiency can be important. Thus, receptors and/or ancillary genes are evolved until an excess of recipient cells bearing the evolved genes are infected by virus at an efficiency of about $10^{-6}$, $10^{-4}$, $10^{-2}$ or 1 infections per viral particle.

V. Evolution of Viruses

The invention further provides methods of evolving viruses to infect cells previously substantially insusceptible to viral infection. Viruses can also be evolved to change the nature of their infection (e.g., from lytic to lysogenic to permanent dormancy or vice versa). The methods of evolving viruses are closely analogous to the methods of evolving sequences for inclusion in DNA vectors to stimulate uptake. Viruses can be evolved either sequentially or concurrently with evolution of viral receptors. For example, one could perform one cycle of recombination and screening/selection for a viral receptor, and then use the cells surviving screening/selection in performing a cycle of viral evolution.

The substrates for viral evolution can be whole viral genomes or fragments. Fragments usually include regions thought to be critical to the feasibility and nature of viral infection, such as the viral origin of replication, viral genes involved in DNA replication and/or viral genes that shut down host functions. Often, the precise nature of sequences critical to viral infection is not known, in which case it is preferable to use a complete viral genome. Viruses constitute a repository of natural diversity both within and between viral strains. For example, there are three principal strains of HIV virus, HIV-I, HIV-II and HIV-III, and numerous subtypes of each, strain. Diversity can also be induced by any of the methods discussed above.

A first round of viral recombination can be performed in vitro according to the same principles as described above. If the substrates for recombination are fragments, they should be inserted into a viral genome after recombination. Recombinant viral genomes are then packaged in vitro before screening/selection.

Recombination can also be performed in vivo in either the cell type for which the virus is being evolved to infect or other cell types. If the former, viruses having genomes forming the initial substrates for recombination may be substantially incapable of infecting the cell type, and, if so, should be introduced by some other means, such as chemical transformation or electroporation. The products of recombination are harvested and, if not already constituting viral genomes, are ligated into such genomes in vitro, followed by in vitro packaging. In vivo recombination is simpler if the cell type in which recombination occurs is susceptible to viral infection. In this situation, cells can be infected at high multiplicity with viruses having genomes forming the substrates for recombination. Progeny virus are harvested from the cells including some having recombinant genomes.

The screening/selection step involves infecting the host cells with recombinant viruses. The nature of the screening/selection step depends on whether one wants to evolve viruses that can enter and express genes in a cell or whether one wants to evolve viruses to establish productive infection. If the former, the recombinant viruses should encode a screening/selection marker (see FIG. 6A). Because it is the virus rather than cells that being evolved, there is, in general, no need to use a different marker in different rounds of screening/selection or to render the viruses bearing the marker suicidal. If the goal is to select viruses capable of productive infection, there is no need to include a screening/selection marker. Rather, one simply harvests progeny virus resulting from infection with recombinant virus (see FIG. 6B). The progeny virus are enriched for recombinant viruses that are best evolved for productive infection. Further enrichment for such viruses can be obtained by performing any number of additional rounds of infection with progeny viruses and harvesting a further generation of progeny. Optionally, individual viruses can be compared for burst size, or doubling time, and the best virus(es) selected.

In general, subsequent rounds of recombination and selection follow the same principles as discussed in other methods of evolution. The products of a previous round of replication exist either in the form of progeny viral particles (if the selection is for productive infection) or in the form of intracellular viral DNA (if selection is for a marker). For viral particles, viral DNA can easily be extracted for a subsequent round of in vitro recombination. Alternatively, the viruses can be used to infect a recipient cell at high multiplicity to allow in vivo recombination to occur. For intracellular viral DNA, the next round of recombination can be performed in vivo by introducing further viral substrate (s) into the cell. For example, cells bearing viral genomes surviving screening/selection can be divided into pools and DNA from one pool introduced into the other pool. Ultimately, viral genomes should be recovered from the cells and packaged for the next round of selection. Alternatively, intracellular viral DNA surviving one round of screening/selection can be extracted and the next round of recombination performed in vitro.

Evolved viruses are capable infecting cell types not normally infected by the virus, or of increasing the efficiency of infection of cell types that were previously somewhat susceptible to infection. Depending on the cell type and virus, efficiencies of $10^{-8}$, $10^{-6}$, $10^{-4}$, $10^{-2}$, $10^{-1}$ and 1 infections per virus can be achieved from a few cycles of recombination and selection performed in a few weeks. For example, phage lambda can be evolved to infect mammalian cells, thereby allowing directing cloning of large libraries in such cells.

VI. Evolution of Conjugative Transfer Genes

Conjugation is the transfer of DNA occurring during contact between cells. See Guiney in: *Bacterial Conjugation* (Clewell, ed., Plenum Press, New York, 1993), pp.75–104; Reimmann & Haas in *Bacterial Conjugation* (Clewell, ed., Plenum Press, New York, 1993), at pp. 137–188 (incorporated by reference in their entirety for all purposes). Conjugation occurs between many types of gram negative bacteria, and some types of gram positive bacteria. Conjugative transfer is also known between bacteria and plant cells (*Agrobacterium tumefaciens*) or yeast.

Conjugative transfer is effected by an origin of transfer (oriT) and flanking genes (MOB A, B and C), and 15–25 genes, termed tra, encoding the structures and enzymes necessary for conjugation to occur. The transfer origin is defined as the site required in cis for DNA transfer. Tra genes include tra A, B, C, D, E, F, G, H, I, J, K, L, M, N, P, Q, R, S, T, U, V, W, X, Y, Z, virAB (alleles 1–11), C, D, E, G, IHF, and FinOP. OriT is sometimes also designated as a tra gene. Other cellular enzymes, including those of the RecBCD pathway, RecA, SSB protein, DNA gyrase, DNA polI, and DNA ligase, are also involved in conjugative transfer. RecE or recF pathways can substitute for RecBCD.

The tra genes and MOB genes can be expressed in cis or trans to oriT. Vectors undergoing conjugation also have an origin of replication which is classified as belonging to an incompatibility group such as Inc A, B, C, D, E, F (I–VI), H (I, Y), i (1, 2, 5, ALPHA), J, K, L, M, N, P (ALPHA, BETA, 1 ALPHA, 3, 7, 10, 13) Q, R (H1, H2, H3) S, T, U, W, X, Z. Only vectors from different incompatibility groups can stably co-exist in the same cell. However, when two vectors from the same incompatibility group are transfected into the same cell, the vectors transiently coexist for sufficient time that recombination can occur between the vectors.

One structural protein encoded by a tra gene is the sex pilus, a filament constructed of an aggregate of a single polypeptide protruding from the cell surface. The sex pilus binds to a polysaccharide on a recipient cells and forms a conjugative bridge through which DNA can transfer. This process activates a site-specific nuclease encoded by a MOB gene, which specifically cleaves DNA to be transferred at oriT. The cleaved DNA is then threaded through the conjugation bridge by the action of other tra enzymes.

The general methods described above for evolution of genes conferring competence or encoding viral receptors can also be applied to evolution of one or more tra genes or other genes with direct or indirect roles in conjugative transfer. The goal of evolving tra genes is to increase the frequency of conjugative transfer and/or to increase the range of cell-types between which conjugative transfer can occur. For example, bacterial tra genes can be evolved to mediate conjugative transfer from bacterial to mammalian cells.

Genes encoding conjugative transfer functions (i.e., tra genes and/or MOB genes) can be evolved individually or collectively, and optionally, in combination with other cellular genes with indirect roles in conjugation (e.g., a DNA ligase gene). OriT can be evolved concurrently or sequentially with genes encoding conjugative transfer proteins. It is also possible to evolve a specific subsequence within a tra gene. The variation between initial recombination substrates can be natural or induced as discussed above. Both in vivo and in vitro formats for recombination are possible.

Regardless how performed, a cycle of recombination generates a diverse library of conjugative transfer genes, which are assayed for conjugative transfer activity by an in vivo assay. The screening/selection assay requires cells containing vectors, each encoding a member of the tra gene library. If a segment of a tra gene has been varied in isolation of flanking gene sequences, the recombinant segments are reassociated with the original flanking sequences in the vector. The vector also contains an origin of transfer, and a marker sequence. The vector further contains at least one origin of replication. If transfer between different cell types is contemplated, the vector can contain two origins of replication, one functional in each cell type (i.e., a shuttle vector). Alternatively, if it is intended that transferred genes should integrate into the chromosome of recipient cells, it is preferable that the vector not contain an origin of replication functional in the recipient cells (i.e., a suicide vector).

The oriT site and/or MOB genes can be introduced into a vector by cloning or transposing the RK2/RP4 MOB function (Guiney, *J. Mol. Biol.* 162, 699–703 (1982)), or by cointegrate formation with a MOB-containing plasmid. A convenient method for large plasmids is to use 'Tn5-Mob', which is the Tn5 transposon containing the oriT of RP4. For example, pUC-like mobilizable vectors pK18 and pK19 (Schafer et al. (1995) Gene 145:69–73) are suitable starting vectors for cloning the tra gene library to be evolved.

The cells containing the conjugative transfer gene library should be capable of expressing a full complement of conjugative transfer genes such that conjugative transfer can occur. If all of the conjugative genes are being evolved simultaneously, a library member usually contains each of the genes, and all such genes are present on the vector. In methods in which one or more conjugative transfer genes are varied while other tra genes are kept constant, the genes being varied are present on the vector. The other genes can be present on the vector, or on a second vector or can be part of host chromosomal DNA.

The collection of cells containing vectors encoding a diverse library of conjugative transfer genes (the first collection of cells) are contacted with a second collection of cells for a sufficient period of time for conjugative transfer to occur to some cells in the second collection. Conjugative transfer is generally more highly efficient when performed in solid media. The proportions of the second collection of cells to the first can vary widely but usually the second collection of cells are present in excess. During the contact period, cells from the first collection harboring the conjugative transfer gene library that have the best genes for conjugative transfer preferentially transfer their vectors including conjugative transfer gene(s) and the vector marker to a cell from the second collection of cells. After a suitable contact period, (which can be decreased after successive rounds of recombination to increase the stringency of screening/selection), cells expressing the marker are screened/selected. Usually, as well as screening/selecting for the vector marker, one selects either against the cells from the first collection or for cells from the second collection. This can be achieved either by including a negative selection marker (e.g., HSV-tk, hprt, gpt) in the cells from the first collection or a positive selection marker in the cells from the second collection. The cells from the second collection that survive screening/selection are enriched for vectors encoding the tra genes with the best properties from the tra library.

The format for screening/selecting evolved tra genes is particularly amenable to performing successive rounds of in vivo recombination and screening/selection. For example, in vivo recombination can be achieved by propagating a collection of cells containing vectors encoding a diverse library of tra genes to be evolved as described above. Optionally, some members of the library of conjugative transfer genes can be contained with the host chromosome as well as inserted into the vectors. Simply by propagating the cells, vectors bearing functional conjugative transfer genes are conjugatively transferred between cells where they can undergo recombination with vectors or chromosomes already present in recipient cells. The genes having the best conjugative transfer properties undergo transfer and therefore recombination most frequently. Thus, there is rapid evolution toward the best recombinant forms of tra gene for supporting conjugative transfer.

Although not necessary, recombination is sometimes facilitated by inserting the diverse conjugative transfer gene library into two different kinds of vectors having different incompatibility origins. Each vector should have a MOB function. Use of two such kinds of vectors allows stable coexistence of multiple vectors within the same cell and increases the efficiency of recombination between the vectors.

After allowing transfer and recombination to proceed for a desired period (which will depend on the cell type), screening/selection can be performed without the need to isolate or transfect tra library members. The collection of cells containing conjugative transfer gene library members is contacted with a second population of cells as described above, and cells from the second collection expressing marker transferred from the first collection are screened/selected. The cells from the second collection can then be propagated to allow a further round of conjugative transfer and recombination of vectors.

Figure 7:
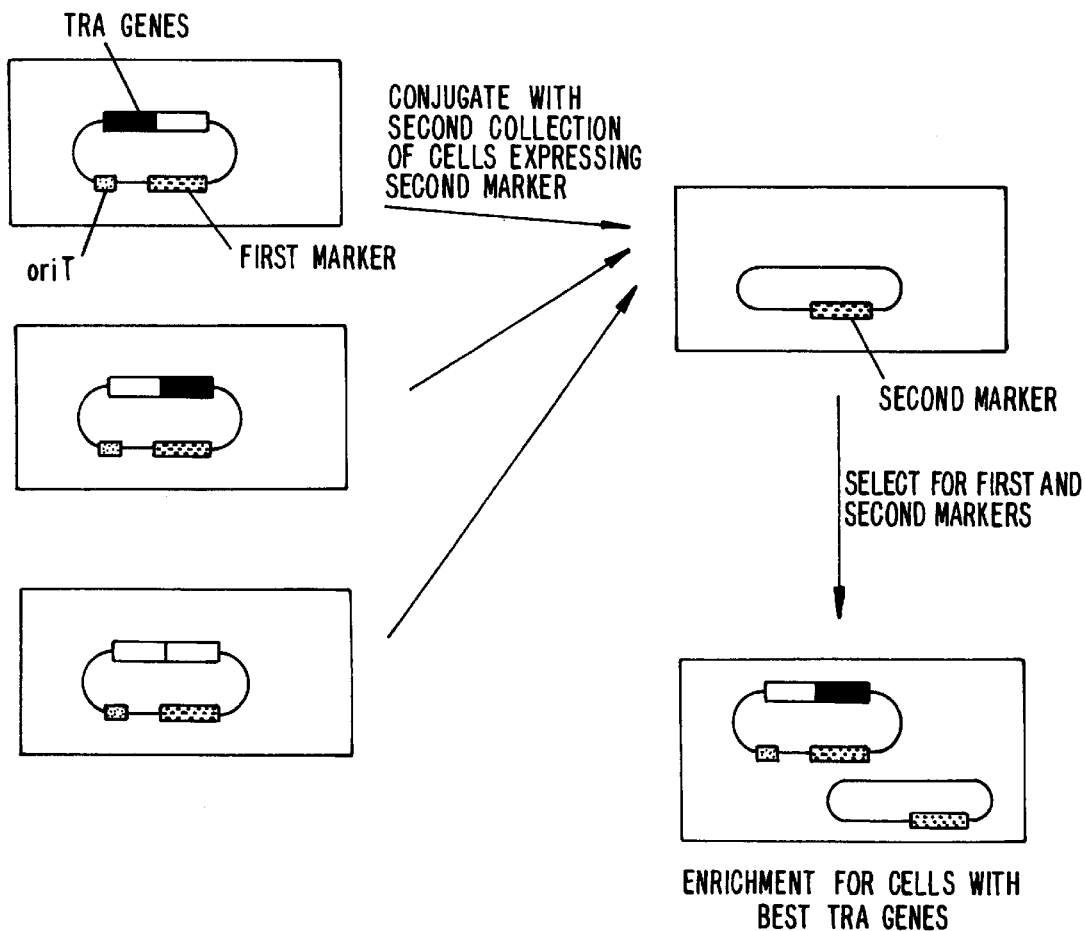
FIG. 7: Scheme for selection of conjugative genes with enhanced conjugative transfer properties.

FIG. 7 shows an exemplary scheme for selection of conjugation gene. The left of the figure shows a first collection of cells containing a library of variant tra genes on a mobilizable vector which also has an oriT site and a marker sequence. The first collection of cells is conjugated with a second collection of cells expressing a second marker as shown in the top right of the figure. Cells expressing both the first and second markers are selected. These cells are enriched for mobilizable vectors containing the best tra genes (i.e., tra genes that mediate intercellular transfer of vectors most efficiently).

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of directing evolution of a virus to increase the efficiency with which it infects a host cell, comprising:

(1) recombining a DNA segment from the virus to be evolved with at least a second DNA segment, the second DNA segment differing from the first DNA segment in at least two nucleotides, to produce a library of recombinant DNA segments;

(2) contacting host cells with a collection of viruses having genomes including the recombinant DNA segments, and screening for viruses that infect the host cells, (3) recombining at least one recombinant DNA segment from a virus infecting the host cells with a further DNA segment, the same or different from the first and second segments, to produce a further library of recombinant DNA segments;

(4) contacting host cells with a collection of viruses having genomes including the further recombinant DNA segments, and screening for viruses that infect the cells, (5) repeating (3) and (4), as necessary, until a virus having a genome including a recombinant segment from a further library infects the host cells with a desired efficiency.

2. The method of claim 1, wherein the host cell is not naturally susceptible to infection by the virus.

3. The method of claim 1, wherein the genome of said virus further comprises a selective marker and the viruses are screened by selecting cells that express the selective marker.

4. The method of claim 1, wherein viruses infecting cells are screened by collecting progeny viruses resulting from infection.

5. The method of claim 1, wherein the host cells are spread in a layer and the viruses are screened by detecting plaques.

6. The method of claim 1, further comprising inserting each recombinant DNA segment into a genome of the virus after a recombination step.

7. The method of claim 2, wherein the DNA segment is a whole viral genome.

8. A method of directing evolution of a virus to increase the efficiency with which it infects a host cell, comprising:

conducting a multi-cyclic polynucleotide extension process on overlapping segments having sequences from a population of variants of a polynucleotide encoding at least part of the genome of the virus under conditions whereby one segment serves as a template for extension of another segment to generate a population of recombinant polynucleotides;

screening or selecting viruses having a genome comprising one of the recombinant polynucleotides for improved inactivity of the host cell relative to the virus.

9. The method of claim 8, wherein the host cell is not naturally susceptible to infection by the virus.

10. The method of claim 8, wherein the polynucleotide encodes a whole viral genome.

11. The method of claim 8, wherein the genome of the virus further comprises a selective marker and the viruses are screened by selecting cells that express the selective marker.

12. The method of claim 8, wherein viruses infecting cells are screened by collecting progeny viruses resulting from infection of the host cell.

13. The method of claim 8, wherein the host cells are spread in a layer and the viruses are screened by detecting plaques.

14. The method of claim 8, further comprising inserting each recombinant polynucleotide into a genome of the virus before the screening or selecting.

* * * * *

UNITED STATES PATENT AND TRADEMARK OFFICE
CERTIFICATE OF CORRECTION

PATENT NO. : 6,096,548
DATED : August 1, 2000
INVENTOR(S) : Willem P. C. Stemmer It is certified that error appears in the above-identified patent and that said Letters Patent is hereby corrected as shown below:

Column 26, line 64, delete "inactivity" and insert --infectivity--

Signed and Sealed this

Twenty-fourth Day of April, 2001

Attest:

NICHOLAS P. GODICI

Attesting Officer     Acting Director of the United States Patent and Trademark Office